United States Patent [19]
Travers et al.

[11] Patent Number: 6,025,399
[45] Date of Patent: Feb. 15, 2000

[54] METHOD OF PRODUCING NEUROMUSCULAR BLOCK BY THE USE OF TETRA-PROPYL OR TETRABUTYLAMMONIUM COMPOUNDS

[75] Inventors: Eva Marianne Travers, Swarthmore, Pa.; Judith Marilyn Dickson, Burlington, Vt.

[73] Assignee: Montefiore Medical Center, Bronx, N.Y.

[21] Appl. No.: 08/950,633

[22] Filed: Oct. 15, 1997

[51] Int. Cl.$^7$ ..................................................... A61K 31/14
[52] U.S. Cl. .............................................................. 514/642
[58] Field of Search ............................................. 514/642

[56] References Cited

U.S. PATENT DOCUMENTS

| | | | |
|---|---|---|---|
| 3,965,178 | 6/1976 | Johnson et al. | 260/567.6 |
| 4,931,593 | 6/1990 | Siray et al. | 564/296 |
| 4,968,433 | 11/1990 | Schmidt et al. | 210/679 |

*Primary Examiner*—Raymond Henley, III
*Attorney, Agent, or Firm*—Hedman, Gibson & Costigan, P.C.

[57] ABSTRACT

A method for inducing neuromuscular blockade is described which is based on the administration to a surgical patient of an amount of a drug comprising tetrabutylammonium or a mixture of tetrabutylammonium and tetrapropylammonium which is effective to induce a neuromuscular block. In addition, there is disclosed the method of combining a non depolarizing muscle relaxant with the tetrabutylammonium or tetraproplyammonium compound to provide a neuromuscular block which requires a reduced dosage of both drugs.

11 Claims, 1 Drawing Sheet

METHOD OF PRODUCING NEUROMUSCULAR BLOCK BY THE USE OF TETRA-PROPYL OR TETRABUTYLAMMONIUM COMPOUNDS

BACKGROUND OF THE INVENTION

The present invention relates to a method of inducing a neuromuscular block for the purpose of facilitating tracheal intubation or for providing muscular relaxation for short lasting surgical procedures.

The time interval between the administration of a muscle relaxant and the development of conditions suitable for the atrumatic intubation of the trachea is the most dangerous phase of anesthesia. During this period, regurgitation and aspiration of gastric contents into the respiratory tract may occur. The aspiration of gastric contents will interfere with adequate oxygenation partly by obstruction of the tracheobronchial tree and partly by bronchiolar constriction caused by the irritating effect of the acid gastric contents his may have serious consequences especially in patients, whose myocardial or cerebral oxygenation is compromised by pathological changes. Obstruction of the upper airway by the partially paralyzed tongue and pharangeal muscle may also contribute to the impairment of respiration. Bronchopneumonia or pneumonitis may be delayed complications of aspiration of gastric contents. For these reasons, it is desirable that the time interval between the administration of a muscle relaxant and tracheal intubation should be as short as possible.

It is also desirable that the duration of a neuromuscular block should conform to the requirements of the surgical procedure and that myoneural activity should be restored rapidly to a normal condition, preferably without the use of an antagonist drug, when there is no longer a need for muscular relaxation.

In the prior art succinylcholine was used clinically for this purpose but experience has shown that succinyl choline has serious undesirable side effects which may cause serious complications which contradict its use in infants and children.

It is known that tetraethylammonium antagonizes the neuromuscular effect of d-tubocurarine and decamethonium in cats but the hypotensive effects of tetraethylammomnium precluded its clinical use for this purpose. It is also known that tetrabutylammonium antagonizes neuromuscular block caused by the depolarizing muscle relaxant decamethonium bromide, and that the neuromuscular antagonist activity of tetrabutylammonium bromide is 20 to 50 times greater than tetraethylammonium.

SUMMARY OF THE INVENTION

The present invention is based on the discovery tetrabutylammonium alone or in combination with tetrapropylammonium will have non depolarizing neuromuscular blocking properties and these compounds may be used to induce a neuromuscular block in a surgical patient to facilitate surgical procedures without causing unfavorable circulatory effects. This discovery shows that these compounds are unique among the tetraalkylammonium compounds.

The tetraalkylammonium compounds may be defined as those are of the Formula I:

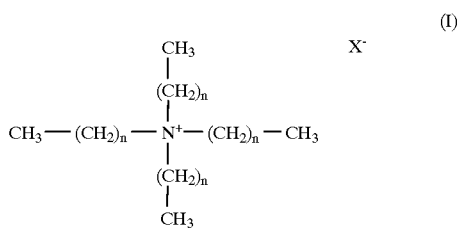

where n is a whole integer of 0–7 and X is a halogen selected from chloro, iodo and bromo. If no counterion is noted for a particular tetraalkylammonium compound, it will be understood that the chloride is the counterion.

Accordingly, it is an object of the invention to provide a method for temporarily inducing a neuromuscular block in connection with surgical procedures.

It is also an object of the invention to provide a method for inducing muscle relaxation to permit the relaxation of the muscles of the jaw, pharynx and larynx to permit intubation of the trachea.

These and other objects of the invention will become apparent from a review of the appended specification.

DETAILED DESCRIPTION OF THE INVENTION

Figure 1:
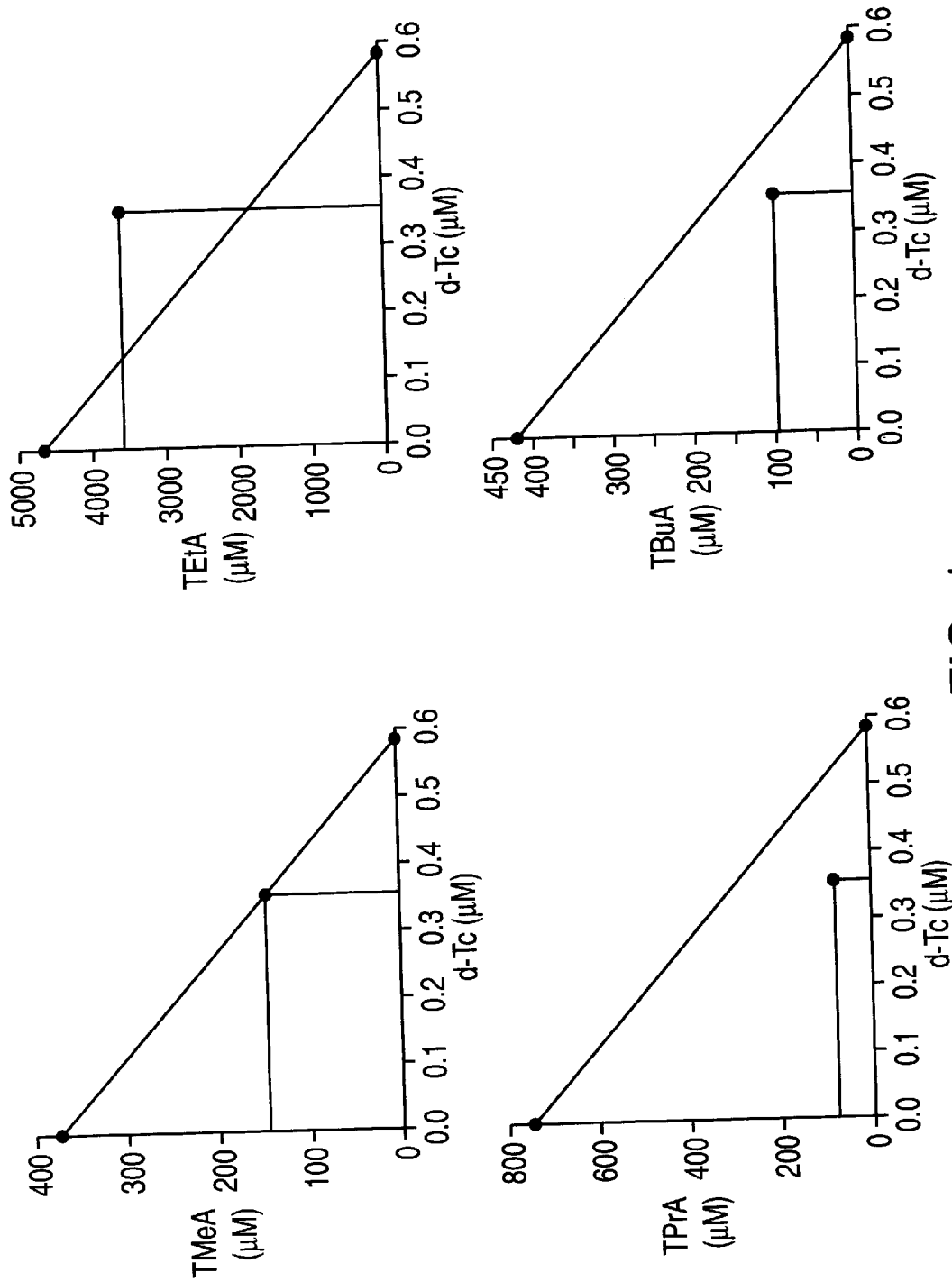
FIG. 1 comprises four isobolgrams which show the results obtained by the combined administration of a non depolarizing muscle relaxant and various tetraalkylammonium compounds.

The compounds of Formula I where n=0 (tetramethylammonium); n=1 (tetraethylammonium); n=2 (tetrapropylammonium); or n=3 (tetrabutylammonium) are soluble in water. Higher members of the group where n=4 (tetrapentylammonium); n=5 (tetrahexylammonium); n=6 (tetraheptylammonium; or n=7 (tetraoctylammonium) are insoluble in water but form colloidal solutions in mixtures of 10% methanol and 90% water. While all of these compounds have the ability to induce neuromuscular blockade, the compound when n=3 has the most favorable relationship between the neuromuscular effects and the circulatory effects drug which permits its use in clinical practice.

The compounds of the invention may be administered parenterally for the purpose of immediately inducing sufficient muscle relaxation to permit atraumatic intubation of the trachea of a patient or the performance of other surgical procedures. The usual dose will be 20 to 100 mg/kg of body weight, preferably 60 to 90 mg/kg of body weight. The dose will be determined by the response of the patient to the particular drug and may be adjusted accordingly. If the tetrabutylammonium and tetrapropylammonium compounds are administered as a mixture, the weight ratio of the compounds will be about 60:40 to 40:60 given according to the dosage set forth above. The preferred route of administration is by intravenous injection and the preferred vehicle is sterile water for injection which may be made isotonic by the addition of effective amounts of salts such as sodium chloride and the like.

The effect of the compounds of the invention may be reversed by discontinuing the administration of the drug and allowing the body to eliminate the drug.

The invention also includes the use of the tetrabutylammonium compound in combination with a non depolarizing muscle relaxant. The term non depolarizing muscle relaxant is used in the context in which that term is used in Anesthesia, 4th Ed., Vol. 1, R. Miller, pp430–431, which is incorporated by reference. Compounds which are non depolarizing muscle relaxants include d-tubocurarine, rocuronium, vercuronium and pipecuronium. The combination of the tetrabutylammonium compound in with a non depolarizing muscle relaxant may be used sequentially or simultaneously. As used herein, sequentially means the drugs are administered with 1 second to 10 minutes of one another. For convenience, a composition of both of these drugs may be formulated which permits the simultaneous administration of both drugs. The composition will contain sufficient amounts of each drugs to induce a temporary neuromuscular block when the drugs are administered by intravenous injection. Generally, the amount of the non depolarizing muscle relaxant present in the composition will be sufficient to provide a dose of about 0.2 to 1.0 mg/kg depending on the potency of the particular non depolarizing muscle relaxant and the amount of the tetrabutylammonium compound administered will be sufficient to provide a therapeutic dose using the doses of the tetrabutylammonium compound set forth above.

solution kept at 37° C. and aerated with 95% $O_2$-5% $CO_2$. The pH of the solution was 7.38–7.42. The phrenic nerves were placed on bipolar, platinum electrodes, immersed in the bath. The nerves were stimulated by supramaximal square wave impulses of 0.2 ms duration administered, depending on the experimental conditions at 0.1, 1, 2, 3 or 5 Hz. Occasionally, trains of 4 stimuli were administered at 2 Hz for 2 seconds. The optimal resting tension of the muscle was determined. Drugs were administered when the preparations had been stabilized.

The EC50 and EC90 values of the compounds were determined from the cumulative log dose-response regression lines. Increments of the various compounds were added to the bath until >90% neuromuscular block developed. The stimulation rate was 0.1 Hz in these experiments and the cumulative ED50 and ED90 of tetramethylammonium, tetraethylammonium, tetrapropylammonium and tetrabutylammonium on the rat-hemidiaphragm was determined as reported in Table 1.

TABLE 1

The In Vitro Neuromuscular Potencies of the Lower Members of the Tetra-alkylammonium Compounds Alone, or Preceded by d-Tubocurarine[1]

| | Alone | | Preceded by d-Tc[2] | |
|---|---|---|---|---|
| Compound | EC50 ($\mu$M) | EC90 ($\mu$M) | EC50 ($\mu$M) | EC90 ($\mu$M) |
| Tetramethylammonium | 251.0 ± 2.2[3] | 375.0 ± 2.0 | 70.9 ± 0.6 | 141.8 ± 3.0 |
| Tetraethylammonium | 4001 ± 210 | 4578 ± 70 | 3496 ± 3 | 3550 ± 1 |
| Tetrapropylammonium | 522.8 ± 4.5 | 774.2 ± 4.6 | 34.7 + 0.5 | 70.8 ± 0.6 |
| Tetrabutylammonium | 334.6 ± 2.3 | 418.8 ± 0.8 | 54.7 ± 0.8 | 95.3 ± ).5 |

[1]Rat phrenic nerve-hemidiaphragm preparation
[2]d-Tc 0.35 $\mu$M, that cause about 20% NM block
[3]Mean ± SEM (n=8–12)

It has been noted that the results of the combined administration of the non depolarizing muscle relaxant with the tetrabutylammonium compound or the tetrapropylammonium compound potentiates the effect of drugs or provide synergistic results when compared to the results obtained by the combined administration of the tetramethylammonium compound or the tetraethylammomnium compound with a non depolarizing muscle relaxant. When synergistic mixtures are present, it is possible to reduce the dose of each of the drugs in the combination by about 10 to 20% by weight or more depending on the particular drug. The data which shows the synergistic results of the combination which includes a tetrabutylammonium or tetrapropylammonium compound is set forth on FIG. 1 where isobolograms have been constructed from the data of Table 1. These isobolograms show that the use of both the tetrabutylammonium and tetrapropylammonium compounds with t-tubocurarine at the dose tested are synergistic and the use of tetramethylammonium and tetraethylammonium with d-tubocurarine are not synergistic.

The effectiveness of the methods of the invention has been demonstrated by in vivo and in vitro pharmacodynamic studies which compared tetrabutylammonium and tetrapropylammonium with other tetraalkylammonium compounds.

Male Sprague-Dawley rats of 275 to 350 g or Harley guinea pigs of 300 to 450 g of body weight were lightly anesthetized with halothane and when they lost their righting reflex, they were decapitated. The rib ends of the two hemidiaphragms, with the phrenic nerves attached, were fixed to the bottom of organ baths and their tendons to FT03 transducers. The baths were filled with modified Krebs'

The order of potencies shown in Table 1 is tetramethylammonium>tetrabutylammonium>tetrapropylammonium>tetraethylammonium.

Using twitch tension as the parameter of evaluation, it was demonstrated that the neuromuscular blocking action of the tetraalkylammonium compounds can be reversed by washout. The administration of neostigmine does not antagonize the neuromuscular effect of tetrabutylammonium but the administration of 1.0 mg/kg of body weight of 4-aminopyridine does antagonize the neuromuscular effect of tetrabutylammonium. This shows that the mechanism of action for each of these drugs is different. The data for the reversal of the neuromuscular block produced by the tetraalkylammonium compounds is set forth in Table 2.

TABLE 2

In vitro Reversal of the Neuromuscular Block Produced by Tetra-alkyl Substituted Ammonium Compounds, by Washout, Neostigmine or 4-Aminopyridine (4-APY) in Rats

| | Twitch Tension (% of Control) | |
|---|---|---|
| Compound | Reversal[1] | Washout |
| Tetramethylammonium | 8.4 ± 0.4 | 106.9 ± 2.05 |
| Tetraethylammonium | 8.4 ± 6.5 | 103.5 ± 0.3 |
| Tetrapropylammonium | 8.8 ± 0.4 | 111.7 ± 5.4 |
| Tetrabutylammonium | 8.8 ± 0.1 | 121.8 ± 3.3 |

TABLE 2-continued

In vitro Reversal of the Neuromuscular Block
Produced by Tetra-alkyl Substituted Ammonium Compounds,
by Washout, Neostigmine or 4-Aminopyridine (4-APY) in
Rats
After[2]

| Compound | Neostigmine[3] | 4-APY[4] | 4-APY + Washout |
|---|---|---|---|
| Tetramethylammonium | 60.9 ± 2.5 | 114.9 ± 3.8 | 148.8 ± 4.4 |
| Tetraethylammonium | NE[5] | NE | 157.5 ± 1.9 |
| Tetrapropylammonium | NE | 128.2 ± 0.6 | 172.2 ± 0.6 |
| Tetrabutylammonium | NE | 58.4 ± 0.9 | 98.6 ± 2.0 |

[1]Mean ± SEM of 12 experiments
[2]Mean ± SEM of 4 experiments
[3]0.75 μM
[4]4 μM
[5]Not effective Note that except for TBuA block, twitch tension is higher than control after 4-APY followed by washout. (For explanation, see text)

In vivo experiments have demonstrated that the tetraalkylammonium compounds except tetrabutylammonium or a mixture of tetrabutylammonium in admixture with tetrapropylammonium have unfavorable circulatory properties which make the compounds other these compounds unsuitable for development for clinical use. A comparison of the circulatory effects of tetrapropylammonium and tetrabutylammonium is set forth in Table 3.

TABLE 3

The Circulatory Effect of 1.5 × ED90 of
Tetrapropylammonium, 1.5 × ED90 Tetrabutylammonium or that
of the combination of 0.75 × ED90 TPrA and TBuA in Rats

| | Control | At Max. NM Block |
|---|---|---|
| | TPrA (20.8 mg.kg$^{-1}$)[1] (n=6) | |
| Heart Rate (bpm) | 398 ± 11 | 353 ± 13* (89%)[4] |
| Systolic Blood Pressure (mmHg) | 114 ± 3 | 82 ± 5* |
| Diastolic Blood Pressure (mmHg) | 84 ± 5 | 47 ± 3* (56%) |
| Pulse Pressure (mmHg) | 30 ± 4 | 35 ± 5* (118%) |
| | TBuA (31.7 mg.kg$^{-1}$)[1] (n=4) | |
| Heart Rate (bpm) | 333 ± 14 (102%) | 337 ± 14 |
| Systolic Blood Pressure (mmHg) | 107 ± 4 | 121 ± 3* |
| Diastolic Blood Pressure (mmHg) | 81 ± 6 | 99 ± 4* (123%) |
| Pulse Pressure (mmHg) | 27 ± 2 | 21 ± 2* (79%) |
| | TPrA and TBuA (10.4 mgkg$^{-1}$)[2] (15.8 mg.kg$^{-1}$)[2] (n+4) | |
| Heart Rate (bpm) | 408 ± 13 | 378 ± 21 (93%) |
| Systolic Blood Pressure (mmHg) | 78 ± 6 | 78 ± 8 |
| Diastolic Blood Pressure (mmHg) | 56 ± 5 | 56 ± 10 (101%) |
| Pulse Pressure (mmHg) | 22 ± 4 | 22 ± 3 (98%) |

[1]1.5 × ED90
[2]0.75 × ED90
[3]All values are mean ± SEM of number of experiments indicated
[4]% of control
*p<0.05 compared to control The tetramethylammonium compound is more potent than the tetrabutylammonium compound in inducing neuromuscular blocking action as shown in Table 4. The tetrabutylammonium compound permits a recovery in less than two minutes while the tetramethylammonium compound requires a 15 minute period for recovery. The data which shows the relative recovery rates is also set forth in Table 4.

TABLE 4

The In Vivo Neuromuscular Potencies of Tetra-
alkylammonium Compounds in Rats

| Compound | ED50 (mg.kg$^{-1}$) | ED90 (mg.kg$^{-1}$) | Recovery Time |
|---|---|---|---|
| Alone | | | |
| Tetramethylammonium (n=4) | 3.3 ± .27[2] | 6.9 ± 0.72 | |
| Tetraethylammonium (n=2) | 166.40 | 195.00 | |
| Tetrapropylammonium (n=6) | 9.9 ± 0.49 | 13.9 ± 0.70 | |
| Tetrabuylammonium (n=4) | 13.7 ± 0.31 | 21.1 ± 1.58 | |
| Preceded by Pipecuronium[1] | | | |
| Tetramethylammonium (n=4) | — | — | 15 min. |
| Tetraethylammonium (n=2) | — | 1.9 ± 0.05 | 30 min. |
| Tetrapropylammonium (n=6) | 0.6 ± 0.70 | 1.9 ± 0.05 | 4 min. |
| Tetrabuylammonium (n=4) | 1.0 ± 0.06 | 3.0 ± 0.08 | 2 min. |

[1]Pipecuronium was 37 μg.kg$^{-1}$ (0.5 × ED90)

Data which shows the effects of various ammonium compounds on the force of contractear of muscles in the rat are shown in Table 5.

TABLE 5

Concentrations of Tetra-alkylammonium Compounds
Which Cause >90% Depression of the Force of Contraction
of the Rat Indirectly ($P_i$) or Directly ($P_d$) Stimulated
Phrenic Nerve-Hemidiaphragm Preparation

| Ratio Compound | $P_i$ | $P_d$ | Potency $P_i/P_d$ |
|---|---|---|---|
| Tetramethylammonium | 375 | 180,000 | 480 |
| Tetraethylammonium | 4578 | 155,000 | 34 |
| Tetrapropylammonium | 774 | 80,000 | 103 |

TABLE 5-continued

Concentrations of Tetra-alkylammonium Compounds
Which Cause >90% Depression of the Force of Contraction
of the Rat Indirectly ($P_i$) or Directly ($P_d$) Stimulated
Phrenic Nerve-Hemidiaphragm Preparation

| Compound | $P_i$ | $P_d$ | Ratio Potency $P_i/P_d$ |
|---|---|---|---|
| Tetrabutylammonium | 419 | 5,000 | 12 |
| Tetrapentylammonium | 450 | 450 | 1 |
| Tetrahexylammonium | 200 | 200 | 1 |
| Tetraheptylammonium | 100 | 500 | 5 |
| Tetraoctylammonium | 150 | 300 | 2 |
| Benzyltributylammonium | 650 | — | — |

Note that with 2 exceptions, TEtA and TOcA $P_i/P_d$ potency ratio is inversely proportional to the number of $CH_2$ radicals in the substituting alkyl chains. (For explanation, see text)

A comparison of time course of the neuromuscular effect of tetrapropylammonium and tetrabutylammonium is set forth in Table 6. This data shows the superiority of tetrabutylammonium over tetrapropylammonium when these compounds are administered to rats who have been pre-treated with a low dose of pipecuronium.

TABLE 6

The Time Course of the neuromuscular Effect of
Low Doses of Tetrapropyl- or Tetrabutylammonium Preceded
by a Low Dose of Pipecuronium[1] in Rats

|  | TPrA (2.9 mg.kg$^{-1}$) (n=4) | TBuA (4.5 mg.kg$^{-1}$) (n=4) |
|---|---|---|
| Time to 80% block (sec) | 10.6 ± 1.37[2] | 11.4 ± 1.09 |
| Onset time (sec) | 18.1 ± 4.13 | 18.8 ± 2.17 |
| Clinical Duration (min) | 3.4 ± 0.36 | 1.7 ± 0.26 |
| Recovery Index (min) | 1.6 ± 0.12 | 1.5 ± 0.25 |
| Time to Maximal Recovery (min) | 7.0 ± 0.59 | 5.7 ± 0.65 |
| Maximal Recovery (% of control) | 96.4 ± 0.36 | 94.9 ± 3.03 |
| T4/T1 Ratio at Maximal Recovery | 0.95 ± 0.02 | 0.94 ± 0.02 |

[1] Dose of pipecuronium was 37 µg.kg$_{-1}$
[2] All values are means ± SEM of number of experiments indicated

I claim:

1. A composition which comprises amounts of tetrabutylammonium and/or tetrapropylammonium in combination with a non depolarizing muscle relaxant which are sufficient to produce a neuromuscular block.

2. A composition as defined in claim 1 wherein the non depolarizing muscle relaxant is selected from the group consisting of d-tubocurarine, rocuronium, vecuronium and pipecuronium.

3. A composition which comprises a sterile aqueous mixture of tetrabutylammonium and tetrapropylammonium in a ratio of 60:40 to 40:60.

4. A method for inducing neuromuscular blockade which comprises administering to a surgical patient an amount of a drug comprising tetrabutylammonium or a mixture of tetrabutylammonium and tetrapropylammonium which is effective to a induce neuromuscular block.

5. A method as defined in claim 4 wherein tetrabutylammonium is administered to a patient.

6. A method as defined in claim 4 wherein a mixture of tetrabutylammonium and tetrapropylammonium is administered to a patient.

7. A method as defined in claim 4 wherein from 20 to 100 mg/kg of body weight of the drug is administered.

8. A method for inducing neuromuscular blockade which comprises administering to a surgical patient tetrabutylammonium or a mixture of tetrabutylammonium and tetrapropylammonium simultaneously or sequentially with a non depolarizing muscle relaxant in amounts which are effective to induce a neuromuscular block.

9. A method as defined in claim 8 wherein the non depolarizing muscle relaxant is selected from the group consisting of d-tubocurarine, rocuronium, vecurconium and pipercuronium.

10. A method as defined in claim 8 wherein tetrabutylammonium and d-tubocurarine are administered simultaneously.

11. A method as defined in calim 8 wherein tetrapropylammonium and d-tubocurarine are administered simultaneously.

* * * * *